United States Patent [19]
Vojdani et al.

[11] Patent Number: 5,766,859
[45] Date of Patent: Jun. 16, 1998

[54] RIBONUCLEASE L INHIBITOR AS AN INDICATOR OF CHRONIC FATIGUE SYNDROME

[75] Inventors: Aristo Vojdani; Pli Mordechai, both of Los Angeles, Calif.

[73] Assignee: Immunosciences Lab, Inc., Beverly Hills, Calif.

[21] Appl. No.: 783,275

[22] Filed: Jan. 15, 1997

Related U.S. Application Data

[62] Division of Ser. No. 727,708, Oct. 7, 1996.

[51] Int. Cl.$^6$ .................................................. G01N 33/53
[52] U.S. Cl. ........................ 435/7.1; 435/7.92; 435/372; 530/350
[58] Field of Search ................................ 435/7.1, 7.92, 435/372; 530/350

[56] References Cited

U.S. PATENT DOCUMENTS 5,258,369  11/1993  Carter .......................... 514/44

FOREIGN PATENT DOCUMENTS 350151     1/1990   European Pat. Off. .
96/10636   4/1996   WIPO .

OTHER PUBLICATIONS

E. Barker, et al. (1994), Immunologic abnormalities associated with chronic fatigue syndrome. *Clinical Infectious Diseases 18 (Suppl. 1)*:S136–41.

M. Becker–Andre, et al. (1989), Absolute mRNA quantification using the polymerase chain reaction (PCR). A novel approach by a PCR aided transcript titration assay (PATTY). *Nucleic Acids Research*, 17(22):9437–9446.

C. Bisbal, et al. (1995), Cloning and characterization of a RNase L inhibitor. *The Journal of Biological Chemisry* 270(22):13308–13317.

D. Ferbus, et al. (1981), The 2'2' oligoadenylate synthetase has a multifunctional 2'5' nucleotidyl–transferase activity. *Biochemical and Biophysical Research Communications* 100(2):847–856.

G. Floyd–Smith, et al. (1981), Interferon action: RNA cleavage pattern of a (2'–5') oligoadenylate–dependent endonuclease. *Science* 212:1030–1032.

K. Fukuda, et al. (1994), The chronic fatigue syndrome: a comprehensive approach to its definition and study. *Annals of Internal Medicine* 121(12):953–959.

G. Gilliland, et al. (1990), Analysis of cytokine mRNA and DNA: detection and quantitation by competitive polymerase chain reaction. *Proc. Natl. Acad. Sci. USA* 87:2725–2729.

Immunsciences Lab., Inc. (approx. Jun. 1995), new product announcement.

N.G. Klimas, et al. (1990), Immunologic abnormalities in chronic fatigue syndrome. *Journal of Clinical Microbiology* 28(6):1403–1410.

P. Lengyel (1993), Tumor–suppressor genes: news about the interferon connection. *Proc. Natl. Acad. Sci. USA* 90:5893–5895.

T. Lion (1994), Clinical implications of qualitative and qualitative polymerase chain reaction analysis in the monitoring of patients with chronic myelogenous leukemia. *Bone Marrow Transplantation* 14:505–509.

E. Mordechai, et al. (1995), Activation of the interferon–inducible enzymes, 2', 5'–oligoadenylate synthetase and PKR by human T–cell leukemia virus type I rex–response element. *Virology* 206:913–922.

L.J.A. Morrison, et al. (1991), Changes in natural killer cell phenotype in patients with post–viral fatigue syndrome. *Clin. exp. Immunol.* 83:441–446.

S. Pestka, et al. (1987), Interferons and their actions. *Ann. Rev. Biochem.* 56:727–777.

T. Salehzada, et al. (1993), 2',5'–Oligoadenylate–dependent RNase L is a dimer of regulatory and catalytic subunits. *The Journal of Biological Chemistry* 268(11):7733–7740.

P.D. Siebert, et al. (1993), PCR Mimics: competitive DNA fragments for use as internal standards in quantitative PCR. *BioTechniques* 14(2):244–249.

R.H. Silverman, et al. (1982), Control of the ppp(A2'p)$_n$. A system in HeLa cells. *Eur. J. Biochem.* 124:131–138.

R.J. Suhadolnik, et al. (1994), Upregulation of the 2–5A synthetase/RNase L antiviral pathway associated with chronic fatigue syndrome. *Clinical Infectious Diseases* 18(Suppl. 1):S96–104.

D.H. Wreschner, et al. (1981), Interferon action–sequence specificity of the ppp(A2'p)$_n$A–dependent ribonuclease. *Nature* 289:414–417.

A. Zhou, et al. (1993), Expression cloning of 2–5A–dependent RNAase: a uniquely regulated mediator of interferon action. *Cell* 72:753–765.

Bleijenberg et al., Enteroviruses and the chronic fatigue syndrome. *Clinical Infect. Dis.*, 19:860–864, Nov. 1994.

Honda et al., Japanese patients with chronic fatigue syndrome are negative for known retroviruses, *Microbiol. Immunol.*, 37(10):779–784, Dec. 1993.

Suhadolnik et al., Changes in the 2–5A synthetase/RNase L antiviral pathway in a controlled clinical trial with poly(I)–Poly(C12U) in chronic fatigue syndrome, In Vivo, 8:599–604, Nov. 1994.

Merck Manual, 14th Ed., Merck Sharp & Dohme Research Laboratories: Rahway, NJ, p.2177, 1982.

Primary Examiner—Stephen Walsh
Assistant Examiner—Claire M. Kaufman
Attorney, Agent, or Firm—Knobbe, Martens, Olson & Bear, LLP

[57]  ABSTRACT

Chronic fatigue syndrome in an individual is diagnosed by determining the level of RNase L inhibitor mRNA or protein in peripheral blood mononuclear cells. Significantly decreased levels of RLI mRNA or protein compared to healthy control individuals indicates the presence of chronic fatigue syndrome.

4 Claims, 3 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

CCACTGAACT TCTGATTCGC                                                                               20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCGTGCTAGC TGGATGTCTT                                                                               20

( 2 ) INFORMATION FOR SEQ ID NO:3:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGATCCCCGC AAGTGAAATC TCCTCCGTCT TGGAGAAGGG AGAGCGTTTG CCCCAGCCAC        60

CCATTTGTAC CATTGATGTG TACATGATCA TGGTCAAATG CTGGATGATT GATGCAGACA       120

GCCGTCCCAA GTTCGTGAG CTGATTGCAG AGTTCTCCAA AATGGCTCGT GACCCTCCCC        180

GCTATCTTGT TATACAGGGA GATGAAAGGA TGCACTTGCC TAGCCCTACA GATTCCAAGT       240

TTTATCGCAC CCTGATGGAG GAGGAGGACA TGGAAGACAT TGTGGATGCA GATGAGTATC       300

TTGTCCCACA CCAGGGCTTT TTCAACATGC CCTCTACATC TCGGACTCCT CTTCTGAGTT       360

CATTGAGCGC TACTAGCAAC AATTCTGCTA CAAACTGCAT TGACAGAAAT GGGCAGGGGC       420

ACCCTGTGAG GGAAGAGGCT TCCTGCCTGC TCCAGAGTAT GTAAACCAGC TGATGCCCAA       480

GAAACCATCT ACTGCCATGG TCCAGAATCA AATCTACAAC TTCATCTCTC TCACAGCAAT       540

CTCAAAGCTC CCCATGGACT CAAGATACCA GAATTC                                 576

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCCCCTTTGG CGCCTTATCA ATTGCGCAAG TGAAATC                                                            37

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTTTCGAGGG GTACCTGAGT TCGCGGATAC CTCAACAGTG ATACGG                                                  46

( 2 ) INFORMATION FOR SEQ ID NO:6:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GGACACGTAG AGGTCTTGAA GATTCCGCAA GTGAATAAAT CTCCTCCG                48
```

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
CAATATGTCC CTCTACTTTC CAATACTGTC GCTCCGCCTT AATAC                  45
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Asp Lys Cys Lys Pro Lys Lys Cys Arg Gln Glu Cys Lys Lys Ser
 1               5                  10                  15
```

RIBONUCLEASE L INHIBITOR AS AN INDICATOR OF CHRONIC FATIGUE SYNDROME

This application is a divisional of U.S. patent application Ser. No. 08/727,708, filed Oct. 7, 1996.

FIELD OF THE INVENTION

The present invention relates to the diagnosis of chronic fatigue syndrome (CFS) by detecting elevated levels of mRNA. More specifically, the invention relates to the diagnosis of CFS by detection of RNase L inhibitor (RLI) mRNA. The RLI gene product is a component of the interferon-mediated antiviral pathway.

BACKGROUND OF THE INVENTION

Chronic Fatigue Syndrome (CFS) is a systemic disorder defined by the Centers for Disease Control (CDC) as self-reported persistent or relapsing fatigue lasting six or more months (Fukuda et al., *Ann. Intern. Med.*, 121:953–959, 1994). Patients with CFS tend to have individualistic symptoms triggered by stress or unknown factors including low grade fever, sore throat, headache, painful lymph nodes, muscle weakness, irritability, inability to concentrate, depression, irregular heartbeat and neuropsychological problems. Although the precise nature and cause of CFS is unknown, there is some clinical and serological association with all of the human herpes viruses, particularly Epstein-Barr virus (EBV) and Human B-lymphotropic virus (HBLV). CFS may involve physiological manifestations of neurological influences on immune function by neurohormones or other immunomodulators of T-lymphocyte function. Upon binding to various lymphocyte surface antigens, viruses induce secretion of lymphokines which may interfere with immune response regulation including mucosal, humoral and cellular immunity.

Many reports have described a decrease in natural killer (NK) cell-mediated cytotoxic activity and abnormal production of tumor necrosis factor-$\alpha$ (TNF-$\alpha$), interleukin-1$\alpha$ (IL-1$\alpha$) and interferon (IFN) (Klimas et al., *J. Clin. Microbiol.*, 28:1403–1410, 1990; Morrison et al., *Clin. Exp. Immunol.*, 83:441–446, 1991; Barker et al., *Clin. Infect. Dis.*, 18:S136–S141, 1994). The interferons are a family of antiviral and antiproliferative cytokines which exert their pleiotropic effects through the induction of several antiviral genes (Lengyel, *Proc. Natl. Acad. Sci. USA*, 90:5893–5895, 1993; Pestka et al., *Annu. Rev. Biochem.*, 56:727–777,1987). The 2-5-oligoadenylate (2-5A) system is an IFN-regulated, double stranded RNA (dsRNA) dependent pathway which controls viral replication and cellular RNA stability. This pathway is summarized in FIG. 1. The primary enzyme in the 2-5A system is a 2-5 oligoadenylate synthetase (2-5OAS) which converts ATP to 2'-5' linked 2-5A oligomers (ppp(A2'p)$_n$), via a 2', 5' phosphodiester bond in the presence of dsRNA (Ferbus et al., *Biochem. Biophys. Res. Commun.*, 100:847–856, 1981; Mordechai et al., *Virology*, 206:913–922, 1995). Subnanomolar concentrations of 2-5A activate a latent endonuclease, RNase L, which is the terminal enzyme in the 2-5A system (Zhou et al., *Cell*, 72:753–765, 1993). Activated RNase L degrades mRNA and rRNA on the 3' side of a UpNp sequence, resulting in inhibition of viral and cellular protein synthesis (Floyd-Smith et al., *Science*, 212:1029–1032, 1981; Wreschner et al., *Nature*, 289:414–417, 1981).

Elevated cellular levels of 2-5A and specific rRNA cleavage products are correlated with inhibition of encephalomyocarditis virus (EMCV) replication in IFN-treated cells, indicating that the antiviral and cytoprotective effect of IFN is partially mediated by the 2-5A system (Wreschner et al., ibid.; Silverman et al., *Eur. J. Biochem.*, 124:131–138, 1982). Introduction of 2-5A into cells inhibited cellular growth rates, implicating the involvement of the 2-5A system in the antiproliferative action of IFN. Increased concentrations of 2-5A and increased RNase L activity have also been observed in individuals with CFS (Sudaholnik et al., *In Vitro*, 8:599–604, 1994).

RNase L is also regulated by a 68 kDa RNase L inhibitor (RLI) which binds to RNase L and inhibits the binding of 2-5A to RNase L (Bisbal et al., *J. Biol. Chem.*, 270:13308–13317, 1995). RLI mRNA levels are not regulated by IFN, although IFN treatment of cells resulted in a three fold increase in RNase L and 2-5 OAS mRNA levels.

There is currently no reliable diagnostic method for CFS. The difficulty associated with establishing such a system and the consequent lack of uniformity in patient samples studied, constitute major impediments in the development of a treatment for CFS. The present invention provides such a diagnostic method for CFS.

SUMMARY OF THE INVENTION

One embodiment of the present invention is a method for diagnosing chronic fatigue syndrome (CFS) in an individual, comprising:

- isolating peripheral blood mononuclear cells (PBMC) from the individual and from a healthy control individual;
- determining the amount of RNase L inhibitor mRNA present in the PBMC from the CFS individual and from the healthy individual; and
- comparing the amount from the CFS individual to the amount from the control individual, wherein a statistically significant decrease in the amount in the CFS patient compared to the control individual indicates the presence of CFS.

Preferably, the determining step comprises quantitative competitive polymerase chain reaction or Northern blotting.

Another embodiment of the invention is a method for diagnosing chronic fatigue syndrome (CFS) in an individual, comprising:

- isolating peripheral blood mononuclear cells (PBMC) from the individual and from a healthy control individual;
- determining the amount of RNase L inhibitor protein in the PBMC from the CFS individual and from the healthy individual; and
- comparing the amount from the CFS individual to the amount from the control individual, wherein a statistically significant decrease in the amount in the CFS patient compared to the control individual indicates the presence of CFS.

Preferably, the determining step comprises Western blotting or ELISA.

DETAILED DESCRIPTION OF THE PREFERRED EMBODIMENTS

Figure 1:
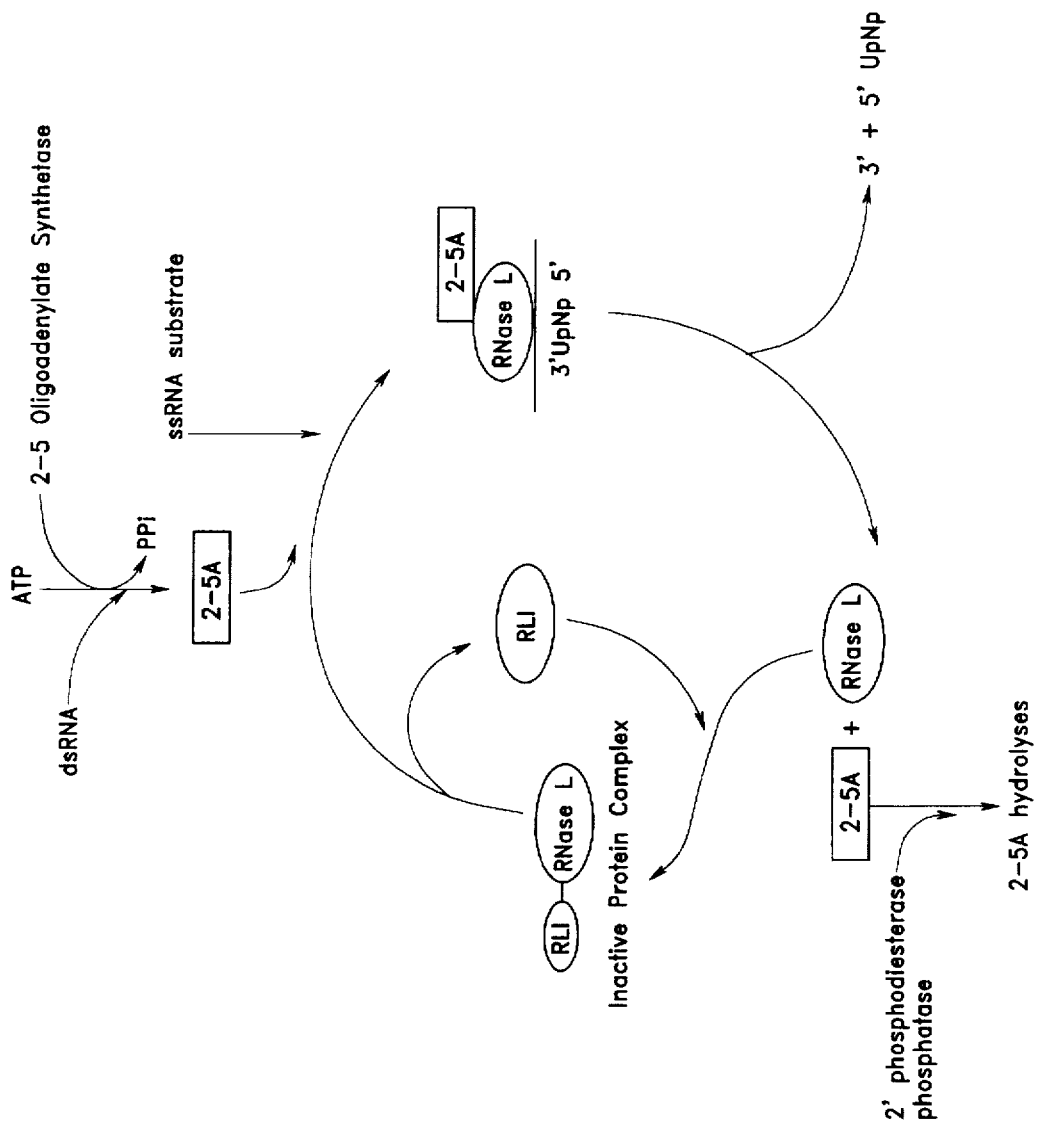
FIG. 1 is a schematic diagram showing the 2-5 oligoadenylate synthetase pathway. RLI=RNase L inhibitor; 2-5A= 2', 5'-oligoadenylates.

The present invention includes the unexpected discovery that levels of RLI mRNA and RLI protein are significantly down-regulated in lymphocytes of CFS patients compared to unaffected individuals. In the examples described below, RLI mRNA levels were determined by performing quantitative competitive PCR (Q/C PCR) on PCR-synthesized cDNA using mRNA isolated from CFS or normal human lymphocytes. The Q/C PCR analysis we conducted indicates a statistically significant decrease in RLI mRNA present in the peripheral blood mononuclear cells (PBMC) of patients with CFS as compared to RLI mRNA levels present in PBMC of healthy individuals. Although the specific examples for the detection of RLI mRNA levels were performed using Q/C PCR, one of ordinary skill in the art will appreciate that any other method capable of detecting RLI mRNA levels is also within the scope of the present invention. One such method is conventional Northern blotting, in which either total RNA or mRNA is isolated from PBMCs of an individual suspected of having CFS. The RNA is analyzed by agarose gel electrophoresis, transferred to a nitrocellulose, nylon or other suitable membrane and incubated with a labeled probe complementary to a region of the RLI mRNA sequence. Because the RLI cDNA sequence is known, such probes can easily be determined and synthesized according to well known methods.

The levels of RLI protein present in the PBMCs of individuals suspected of having CFS can also be determined using an immunoassay. Therefore, we have used a polyclonal antibody generated against RLI in conjunction with conventional detection techniques such as Western blotting and enzyme-linked immunosorbent assay (ELISA). In particular, in Example 8, polyclonal antiserum specific for RLI has been produced which can be used to detect RLI protein levels by such methods.

Although differences in RLI mRNA and protein levels are observed in CFS versus healthy individuals, no such differences in RNase L levels are observed. RLI mRNA deficiency in CFS patients may explain the increase in RNase L activity in CFS patients. The increased activation of RNase L results in a marked increase in cellular RNA turnover and constant 2',5' polymerization of ATP due to the virtually constitutive activation of the 2-5A pathway, resulting in general fatigue, myalgia and muscle weakness. RNase L, once activated, controls viral as well as cellular mRNA degradation. Unlike 2-5OAS, RNase L mRNA and protein levels do not fluctuate markedly during viral infection (Zhou et al., Cell, 72:753–765; Salehzada et al., J. Biol. Chem., 268:7733–7740). RNase L is regulated post-transcriptionally by 2-5A molecules which act as an activator (Floyd-Smith et al., Science, 212:1020–1032, 1981; Wreschner et al., Nature, 289:414–417, 1981) and by the formation of a latent heterodimeric protein-protein interaction with RLI (Bisbal et al., J. Biol. Chem.270:13308–13317, 1995 and FIG. 1). In addition to bioactive 2-5A, the control of RNase L activity in CFS individuals is most likely due to the intracellular RNase L:RLI protein ratio.

The control of mRNA degradation is a critical element in the regulation of gene expression. The 2-5A system is a major pathway in controlling mRNA turnover via the effector enzyme RNase L. Upon viral infection or activation of the IFN system, only the concentration of RNase L is elevated which may result is deregulation of the equilibrium between RNase L and RLI which promotes activation of the 2-5A system (FIG. 1). The data presented in the examples described below underscore the central role of the 2-5A system in the etiology of CFS.

The following examples provide illustrative methods for carrying out preferred steps in conjunction with the practice of the present invention. As such, these examples are provided for illustration purposes only and are not intended to limit the invention.

PBMCs were isolated from both CFS and healthy individuals as described in the following example.

EXAMPLE 1

Isolation of PBMCs

Twenty-five patients with CFS (15 males, 10 females) and 13 normal control individuals (5 males, 8 females) were used as sources of PBMCs. All subjects met the epidemiological case definition of CFS established by the CDC. Controls were randomly selected volunteers employed by Immunosciences Lab, Inc., Beverly Hills, Calif., or had been seen by physicians for routine physical examinations unrelated to the existence of CFS or any other disorder. Venous blood (10 ml) was obtained by venipuncture. PBMCs were isolated by Ficoll-Hypaque (Sigma, St. Louis, Mo.) gradient centrifugation of heparinized blood at 1,600 rpm for 30 min. as described (Sudaholnik et al., Clin. Infect. Dis., 18:S96–S104, 1994). The lymphocyte ring was isolated, rinsed twice with phosphate-buffered saline (PBS) and stained with Trypan Blue to determine cellular viability.

RNA was isolated from PBMCs as described in the following example.

EXAMPLE 2

Isolation of RNA from PBMCs

RNA was extracted from PBMCs with TRIZOL™ reagent (GIBCO BRL, Gaithersburg, Md.) as described by the manufacturer. Briefly, PBMCs were suspended in 1 ml TRIZOL™ reagent followed by addition of 200 μl chloroform. The cell suspension was shaken in an orbital shaker, then incubated for 10 min at room temperature to allow phase separation. Samples were centrifuged (12,000 rpm, 10 min, 4° C.) and the aqueous phase was transferred to a fresh tube. Isopropanol (500 μl) was added to each tube followed by incubation at −70° C. for 1 hour to precipitate RNA. Samples were centrifuged (12,000 rpm, 20 min., 4° C.) and the resulting RNA pellet was washed with 70% ethanol and dissolved in 10 μl diethyl pyrocarbonate (DEPC)-treated water. One μl was used for spectrophotometric quantitation. The RNA was treated with DNase I (amplification grade, GIBCO BRL) as described by the manufacturer.

Total RNA was converted to cDNA as described below.

EXAMPLE 3

Reverse Transcription Polymerase Chain Reaction (RT-PCR)

Total RNA was converted to cDNA using the GENE AMP™ RNA PCR kit (Perkin-Elmer, Norwalk, Conn.). Each reaction mixture (20 μl total volume) contained 10 μl RNA (approx. 2 μg), 2.5 μM oligo d(T)$_{16}$, 1 mM dNTP, 5 mM MgCl$_2$, 2 μl 10×PCR buffer II, 1 μl MULV RNase inhibitor (10 U/μl) and 2.5 μl MMLV reverse transcriptase (50 U/μl). Reaction mixtures were incubated at 42° C. for 20 min, then at 85° C. for 5 min.

Histone PCR was performed for each sample to serve as internal controls for intersample equivalency of total amounts of RNA analyzed as described below.

EXAMPLE 4

Histone PCR

Aliquots (2 μl) of cDNA prepared according to Example 3 were mixed in a total volume of 50 μl PCR reaction mixture containing 10×PCR buffer (United States Biochemical Corp., Cleveland, Ohio), 3 mM MgCl$_2$, 0.3 mM dNTP, 2.5 μl Taq DNA polymerase (5 U/μl) (U.S. Biochemical) and 1 μl (8 pmol) of 5' and 3' histone amplified primer set 5'-CCACTGAACTTCTGATTCGC-3'(SEQ ID NO: 1) and 5'-GCGTGCTAGCTGGATGTCTT-3' (SEQ ID NO: 2). The histone primers are complementary to the mRNA of constitutively expressed human histone gene H3.3 as described (Pieper et al., *Cancer Commun.*, 2:13–20, 1990). The cDNA was amplified for 30 cycles using the following parameters: 94° C. for 45 sec, 60° C. for 45 sec, 72° C. for 90 sec in a PTC-100 Programmable DNA Thermal Cycler (MJ Research, Inc.). A sample with no added cDNA served as a negative control.

Internal control DNA fragments were synthesized for use in Q/C PCR as described in the following example.

EXAMPLE 5

Synthesis of Internal RLI and RNase L Control DNA Fragments

Q/C PCR is an amplification technique based on a competitive approach using non-homologous internal DNA standards which are DNA fragments constructed for use in competitive PCR amplification for quantitation of target mRNA levels (Gilliland et al., *Proc. Natl. Acad. Sci. U.S.A.*, 87:2725, 1990; Becker-Andre, *Nucl. Acids Res.*, 17:9437, 1989; Siebert et al., *BioTechniques*, 11:244–249, 1993, the entire contents of which are hereby incorporated by reference). Each internal standard consists of a heterologous DNA fragment with primer templates that are recognized by a pair of gene-specific (composite) primers. These templates "mimic" the target and are amplified during PCR. This mimic competes with the target DNA for the same primers and thus acts as an internal standard.

To construct the internal standard, two rounds of PCR amplification are performed. In the first PCR reaction, two composite primers are used, each of which contains the target gene primer sequence attached to a short stretch of sequence designed to hybridize to opposite strands of a "mimic" DNA fragment. The desired primer sequences are thus incorporated during the PCR amplification. A dilution of the first PCR reaction is then amplified again using only the gene-specific primers which ensures that all PCR mimic molecules have the complete gene-specific primer sequences. The size of the PCR mimic can range from 200–650 base pairs, simply by choosing the appropriate sequences of the mimic DNA fragment for the composite primers. Following the second PCR amplification, the PCR mimic is purified by passage through a column.

Serial dilutions of PCR mimics are added to PCR amplification reactions containing constant amounts of the target cDNA sequence. The PCR mimic and target template thus compete for the same primers in the same reaction. By knowing the amount of PCR mimic added to the reactions, the amount of target template and initial mRNA levels can also be determined.

An internal control (mimic) DNA fragment (600 bp) was synthesized using the PCR MIMIC™ construction kit (Clontech, Palo Alto, Calif.) according to the manufacturer's instructions. Briefly, a 576 bp neutral fragment (BamHI/EcoRI fragment of the v-erbB gene) (SEQ ID NO: 3; 4 ng) was used as a template with composite RLI or RNase L primers. RLI primers used were:
5'-GCCCCTTTGGCGCCTTATCAATTGCGCAAGTG-AAATC-3' (SEQ ID NO: 4) and
5'-GTTTCGAGGGGTACCTGAGTTCGCGGATACCTC-AACAGTGATACGG-3'(SEQID NO: 5). RNase L primers used were: 5'-GGACACGTAGAGGTCTTGAAGATT-CCGCAAGTGMTAAATCTCCTCCG-3' (SEQ ID NO: 6) and 5'-CAATATGTCCCTCTACTTTCCAATACTGTCG-CTCCGCCTTAATAC-3' (SEQ ID NO: 7).

PCR reaction mixtures (50 μl) were subjected to 20 cycles of PCR (94° C. for 45 sec, 60° C. for 45 sec, 72° C. for 90 sec) using the target RLI primers in a final reaction volume of 100 μl. The PCR product was purified using a pre-spun Chroma column (Clontech) as described by the manufacturer. The mimic DNA fragment was quantitated by electrophoresis and serial dilutions were prepared for Q/C PCR.

EXAMPLE 6

Quantitative Competitive PCR

Q/C PCR was performed essentially as described (Lion, *Bone Marrow Transplantation*, 14:505–509, 1994). Aliquots (0.2 μg) of cDNA were added to serially diluted mimic DNA. The Q/C PCR reaction mixture (50 μl) contained the synthesized 600 bp RLI mimic DNA, 3 mM MgCl$_2$, 1.25 mM dNTP, 5 μl 10×PCR buffer (10 mM Tris-HCl, pH 8.3, 50 mM KCl, 20 mM MgCl$_2$), 2.5 units Taq DNA polymerase and 7 pmol (1 μl) of the RLI primers (SEQ ID NOS: 4,5) or the RNase L primers (SEQ ID NOS: 6,7). The Q/C PCR reaction mixtures were heated to 94° C. for 3 min and subjected to 30 cycles of PCR (94° C. for 30 seconds, 54° C. for 30 seconds, 72° C. for 60 seconds). Following the final PCR cycle, a 5 min elongation step was performed at 72° C. Aliquots (25 μl) of the PCR reaction were analyzed by electrophoresis on a 3% Nusieve/agarose (3:1)(FMC) gel in the presence of 0.5 μg/ml ethidium bromide. The concentration of the internal standard and RLI PCR products were measured by scanning the ethidium bromide-stained gel using a digital imaging densitometer (Alpha Inotech Corp.). Because the PCR-amplified RLI (712 bp) and RNase L (400 bp) fragments are larger than their internal standard counterparts (600 bp and 275 bp, respectively), they exhibit slower migration on an agarose gel. The concentration ratio of the internal controls divided by the concentration of RLI were plotted against the input concentration of the internal standards per tube. The amount of RLI cDNA present in the reaction mixture was defined as the amount of internal control present where the concentration ratio was equal to the PCR product.

Figure 2:
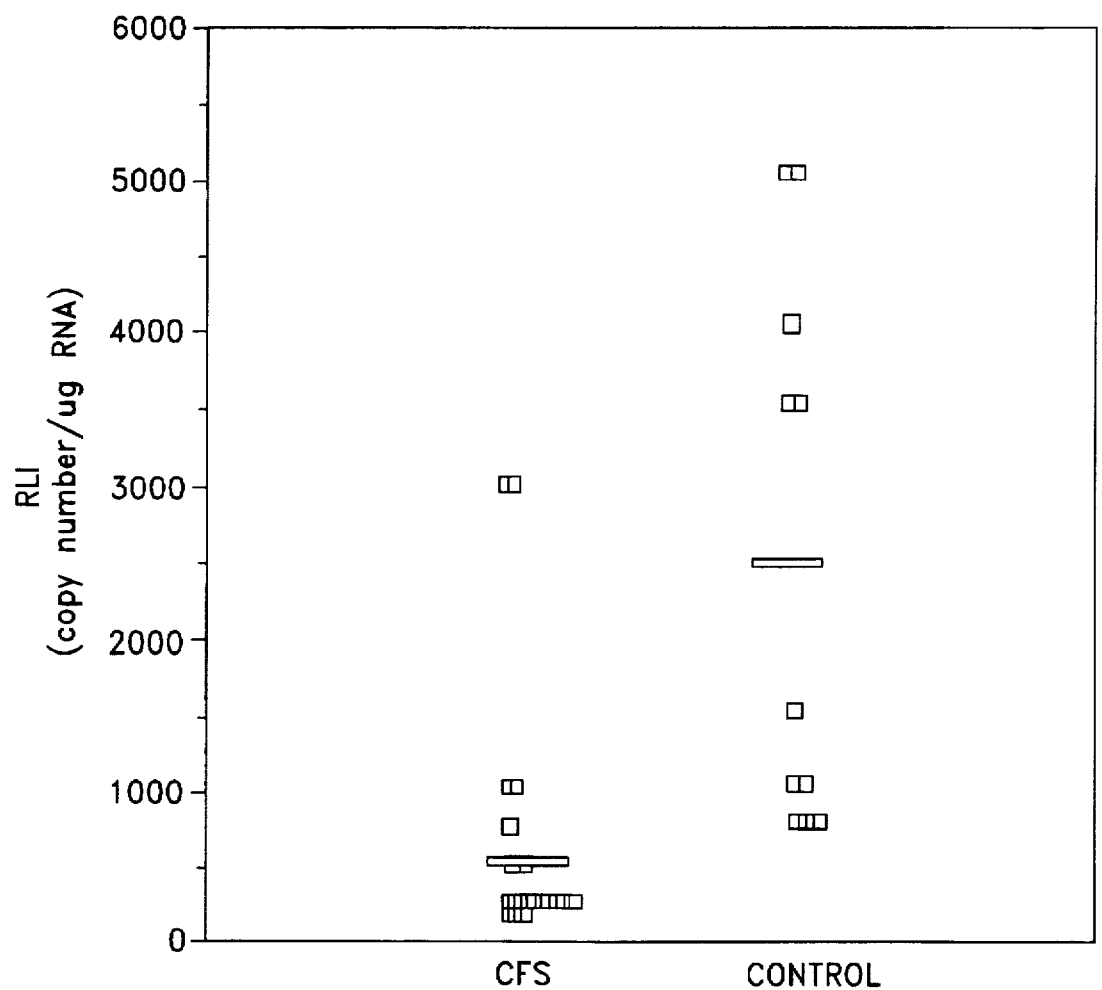
FIG. 2 is a graph comparing the level of RLI mRNA in patients having CFS with control patients. RLI mRNA levels are expressed as copy number per μg total RNA. The horizontal bar indicates the mean for each group.
Figure 3:
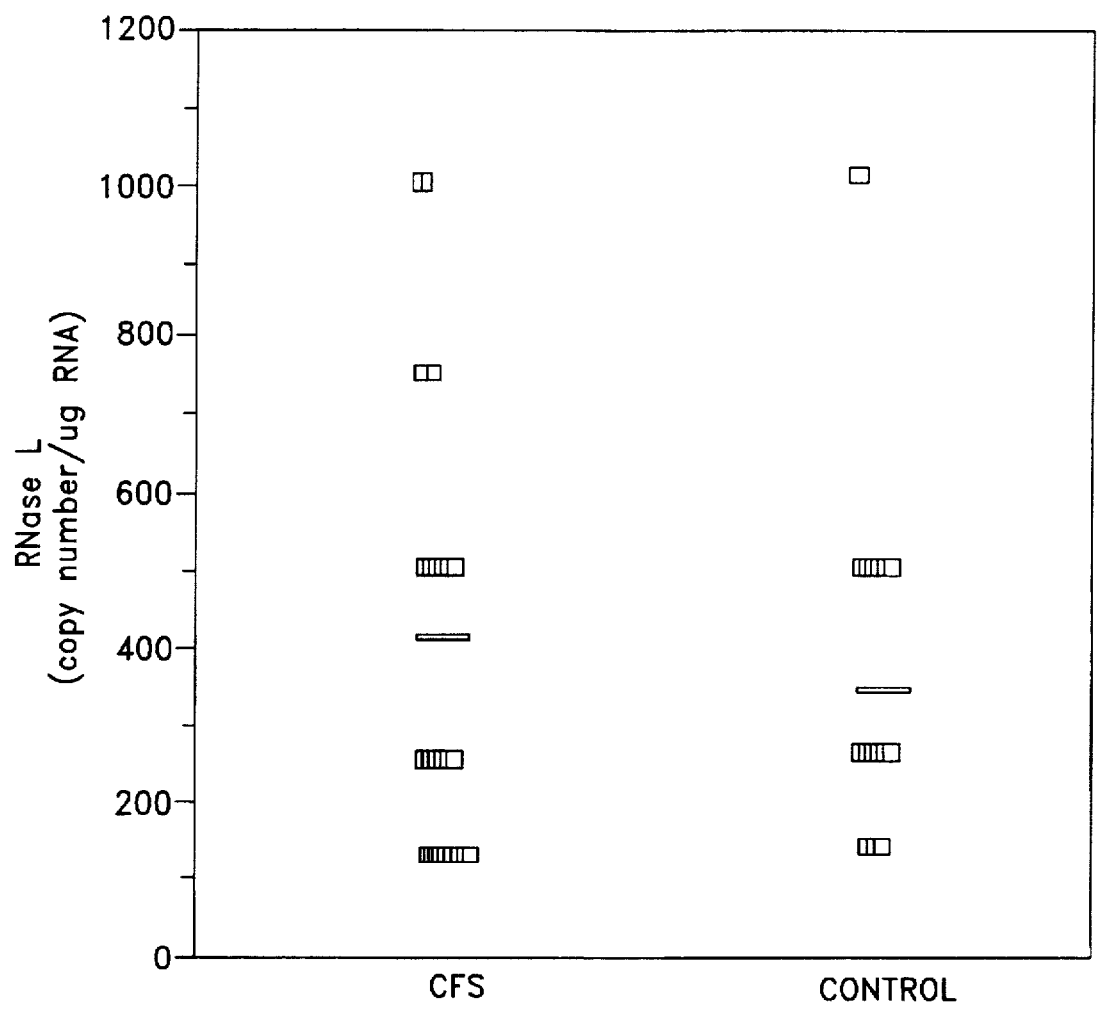
FIG. 3 is a graph comparing the level of RNase L mRNA in patients having CFS as compared to control-individuals. RNase L mRNA levels are expressed as copy number per μg total RNA. The horizontal bar indicates the mean for each group.

RLI mRNA levels in PBMCs from 12 healthy controls ranged from 750 to 5,000 RLI mRNA molecules per μg RNA (mean basal level=2296, S.E.=506). In contrast, the mean value for RLI mRNA present in PBMCs of CFS patients (n=25) was significantly down-regulated compared to control individuals (CFS=569, S.E.=154) (P<0.0001, Mann-Whitney U-Test) (FIG. 2). RNase L mRNA levels in control individuals ranged from 125–1,000 mRNA molecules per µg RNA (mean basal level=356, S.E.=63). The mean value for RNase L mRNA present in PBMCs of CFS patients (n=25) was not statistically different compared to healthy control individuals (CFS=435, S.E.=67) (P<0.1, Mann-Whitney U-Test) (FIG. 3). Histone 3.3 mRNA levels were tested in three normal and four CFS individuals and indicated that the same amount of RNA was analyzed in Q/C PCR.

These results demonstrate the down-regulation of RLI mRNA in CFS patients as compared to healthy controls. CFS patients have increased 2-5OAS activity which results in a marked increase in bioactive 2-5A (up to 220 fold compared to healthy controls) and RNase L activity (Sudaholnik et al., ibid.). The down-regulation of RLI mRNA in CFS individuals may explain the increased RNase L activity observed in CFS patients.

EXAMPLE 7

Detection of RLI mRNA by Northern Blotting

Poly(A)$^+$ RNA is isolated from both control and CFS RNA by oligo(dT)-cellulose chromatography. mRNA is analyzed by electrophoresis on a 1.0% agarose-formaldehyde gel. The mRNA is transferred to a nitrocellulose membrane using a conventional Northern blotting apparatus, followed by prehybridization and hybridization with a $^{32}$P-labeled RLI cDNA probe. The filter is then washed under high stringency conditions and exposed to x-ray film. The resulting bands are quantitated using a scanning densitometer. The results show that RLI mRNA levels are significantly decreased in CFS individuals compared to healthy control individuals.

As described above, CFS can also be diagnosed by evaluating levels of RLI protein. One method of determining these levels involves the use of an immunoassay for the protein. Both polyclonal and monoclonal antibodies can be used; however, polyclonal antibodies are preferred so as to account for antigenic variation among individuals. We prepared polyclonal antibodies as described in the following example.

EXAMPLE 8

Generation of Polyclonal Antiserum Against RLI

The peptide DKCKPKKCRQECKKS (SEQ ID NO: 8), corresponding to amino acids 14–28 of RLI (Bisbal et al., ibid.), was synthesized on an automated peptide synthesizer using methods well known to one of ordinary skill in the art. The peptide was then conjugated to the immunogenic carrier protein keyhole limpet hemocyanin (KLH) with glutaraldehyde. The peptide-KLH conjugate was injected into three Flemish Giants rabbits. Each animal received six subcutaneous injections (100 µg/injection) at six distinct sites. Booster injections were given at 2, 4, 6, 8, 10 and 12 weeks. The rabbits were bled at 10, 11, 12 and 14 weeks and the blood (60 ml/bleed) was centrifuged to pellet blood cells. The remaining serum (25–30 ml) was tested for immunoreactivity against RLI on a Western blot of lymphocyte lysate from CFS patients, as described in the example that follows.

EXAMPLE 9

Detection of RLI by Western Blotting

PBMCs from CFS patients and control individuals are lysed in buffer containing 20 mM HEPES, pH 7.5, 5 mM MgCl$_2$, 120 mM KCl, 10% glycerol, 0.5% Nonidet-P40™ (NP-40) as described (Mordechai et al., Virology, 206:913–922, 1995). Proteins are separated by SDS-polyacrylamide gel electrophoresis (SDS-PAGE). The separated proteins are electrophoretically transferred to nitrocellulose. The nitrocellulose is then incubated with the polyclonal antibody to RLI produced as described in Example 8. The primary antibody is replaced with anti IgG-horseradish peroxidase conjugate (Amersham). Bound secondary antibody-horseradish peroxidase conjugate is detected using chemiluminescence detection reagents (Amersham). There is significantly more RLI present in PBMCs from control individuals compared to CFS individuals.

Any of a variety of other immunoassays can also be adapted to determine RLI protein levels. The following example provides one such assay in the form of an ELISA.

EXAMPLE 10

Detection of RLI by ELISA

Serial dilutions of clarified cell lysate from Example 1 are placed in 96-well microtiter plates and incubated for 3 hours at 37° C. Lysate is removed, and the wells are washed three times with PBS. Polyclonal antibody against RLI is added to the wells and incubated for 1 hour at room temperature. Antibody is removed and the wells are washed several times with PBS. Alkaline phosphatase-conjugated goat anti-rabbit IgG is then added to the wells and incubated for 30 min at room temperature, followed by addition of a colorimetric alkaline phosphatase substrate. The plates are read at on a microplate reader set at the optimum wavelength of the colorimetric reagent. PBMC lysates from CFS individuals contain significantly more RLI than do normal lysates.

It should be noted that the present invention is not limited to only those embodiments described in the Detailed Description. Any embodiment which retains the spirit of the present invention should be considered to be within its scope. However, the invention is only limited by the scope of the following claims.

---

What is claimed is:

1. A method for detecting an increased likelihood of the presence of chronic fatigue syndrome (CFS) in an individual, comprising:

isolating peripheral blood mononuclear cells (PBMCs) from said individual;

determining the amount of RNase L inhibitor (RLI) protein in said PBMCs from said individual; and comparing said amount of RLI protein from said individual to the mean amount of RLI protein in PBMCs from a control individual known not to have CFS, wherein a significant decrease in said amount from said individual compared to said mean amount from said control individual indicates an increased likelihood of the presence of CFS.

2. The method of claim 1, wherein said determining step comprises an immunoassay.

3. The method of claim 2, wherein said immunoassay comprises an ELISA assay.

4. The method of claim 2, wherein said immunoassay comprises Western blotting.

* * * * *